(12) United States Patent
Kaplan

(10) Patent No.: US 9,120,848 B2
(45) Date of Patent: Sep. 1, 2015

(54) NON-AQUEOUS SYNTHESIS OF POLYSACCHARIDE-PROTEIN CONJUGATES FOR VACCINES

(76) Inventor: Harvey Kaplan, Thornhill (CA)

( * ) Notice: Subject to any disclaimer, the term of this patent is extended or adjusted under 35 U.S.C. 154(b) by 0 days.

(21) Appl. No.: 13/240,588

(22) Filed: Sep. 22, 2011

(65) Prior Publication Data

US 2012/0077965 A1      Mar. 29, 2012

Related U.S. Application Data

(60) Provisional application No. 61/385,673, filed on Sep. 23, 2010.

(51) Int. Cl.
| | |
|---|---|
| *C07K 14/00* | (2006.01) |
| *C07K 14/195* | (2006.01) |
| *A61K 38/16* | (2006.01) |
| *A61K 39/02* | (2006.01) |
| *C07K 14/33* | (2006.01) |
| *C07K 14/34* | (2006.01) |
| *A61K 39/00* | (2006.01) |
| *A61K 47/48* | (2006.01) |

(52) U.S. Cl.
CPC ............... *C07K 14/00* (2013.01); *A61K 38/16* (2013.01); *A61K 38/164* (2013.01); *A61K 39/00* (2013.01); *A61K 47/4833* (2013.01); *C07K 14/195* (2013.01); *C07K 14/33* (2013.01); *C07K 14/34* (2013.01); *A61K 2039/555* (2013.01); *A61K 2039/55511* (2013.01); *A61K 2039/55583* (2013.01); *A61K 2039/60* (2013.01); *A61K 2039/6031* (2013.01); *A61K 2039/6087* (2013.01)

(58) Field of Classification Search
CPC ........ C07K 14/00; C07K 14/33; C07K 14/34; C07K 14/195; A61K 38/16; A61K 38/164; A61K 39/00; A61K 2039/555; A61K 2039/55511; A61K 2039/55583; A61K 2039/60; A61K 2039/6031; A61K 2039/6087; A61K 47/4833

USPC ......................................................... 530/395
See application file for complete search history.

(56) References Cited

U.S. PATENT DOCUMENTS 4,356,170 A * 10/1982 Jennings et al. ........... 424/194.1
2006/0122369 A1 * 6/2006 Kaplan et al. ................. 530/322

OTHER PUBLICATIONS

"Preparation of Polysaccharide-Conjugate Vaccines", Methods in Molecular Medicine, vol. 87: Vaccine Protocols, 2nd ed., edited by Robinson, Hudson, and Cranage: 2003 Humana Press Inc., Totowa, NJ.*
Fernandes, "Biopharmaceutical Sialytion", European Biopharmaceutical Review (Spring 2006) pp. 100-104.*
Vogel's Textbook of Practical Organic Chemistry, 5th ed., Longman Scientific and Technical: Essex, England, 1989.*
Vogel, Vogel's Textbook of Practical Organic Chemistry, 5th ed., Longman Scientific and Technical: Essex, England, 1989.*
Peeters et al., "Preparation of Polysaccharide-Conjugate Vaccines", Methods in Molecular Medicine, vol. 87: Vaccine Protocols, 2nd ed., edited by Robinson, Hudson, and Cranage: 2003 Humana Press Inc., Totowa, NJ.*

* cited by examiner

*Primary Examiner* — Karlheinz R Skowronek
*Assistant Examiner* — Catherine Mader
(74) *Attorney, Agent, or Firm* — Adrian M. Kaplan

(57) ABSTRACT

The invention is a novel chemical coupling methodology for the synthesis of a stable polysaccharide-protein conjugates as the immunogenic component for vaccines. A covalent bond is formed between polysaccharide and protein in the dry state in the absence of water and oxygen. A polysaccharide antigen is covalently linked to the protein by activating the polysaccharide with periodate to introduce aldehyde groups into the polysaccharide, lyophilizing an aqueous mixture of a protein and activated polysaccharide, sealing the dry lyophilized mixture in a vessel under vacuum or inert gas and then incubating the sealed vessel at an elevated temperature.

15 Claims, 4 Drawing Sheets

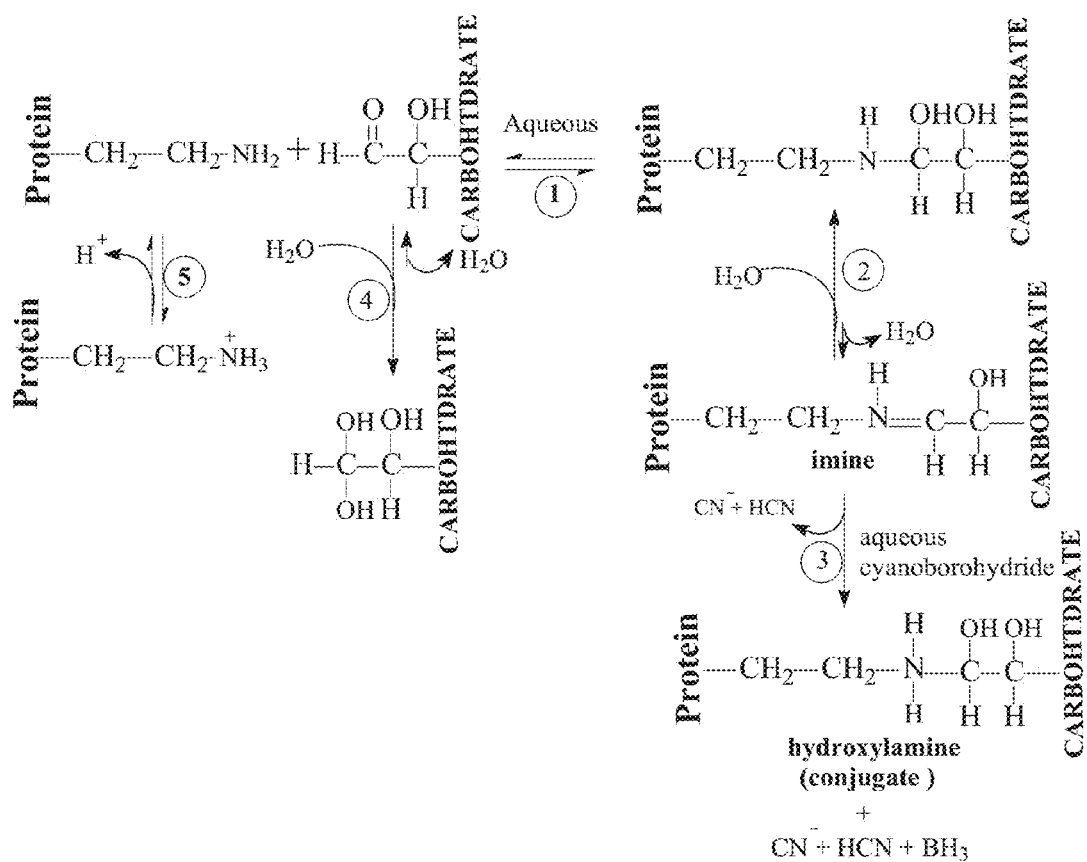
Figure 1. Aqueous Reductive Amination Procedure for Synthesizing Polysaccharide-Protein Conjugate Figure 2. Inventive Vacuum Coupling Reaction
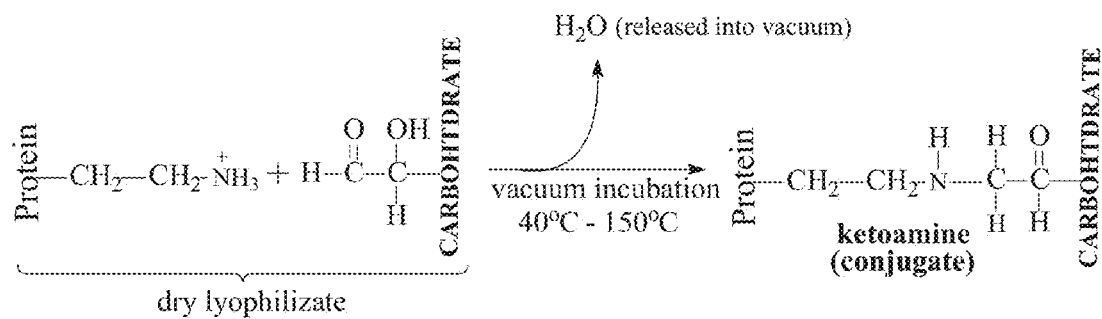

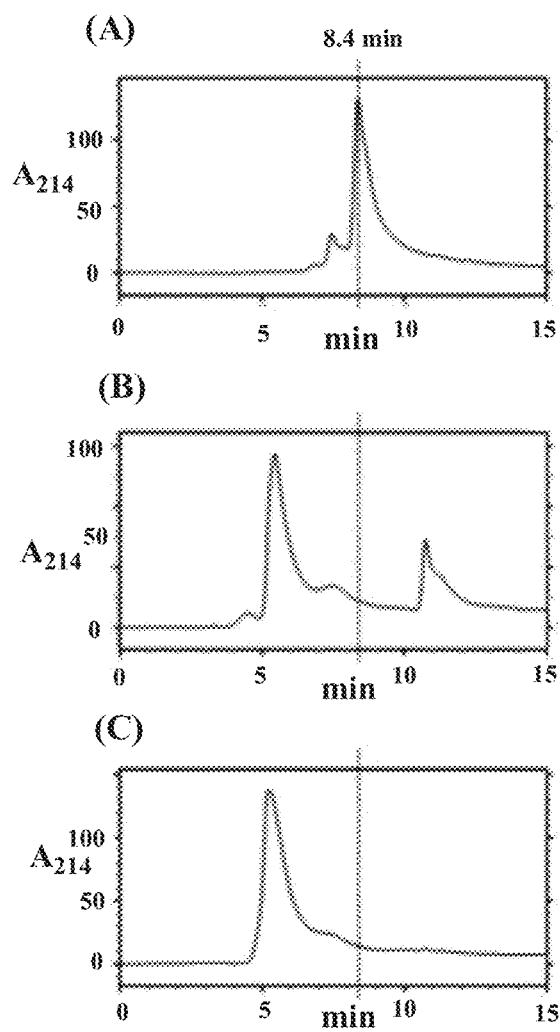
Figure 3. HPLC Profiles

Figure 4. SDS-PAGE
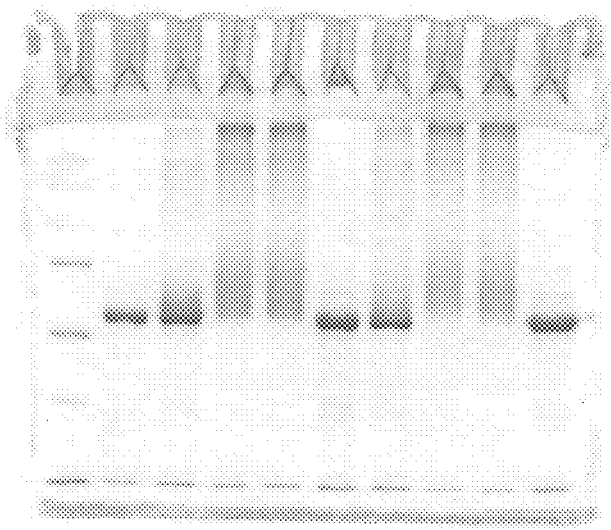

NON-AQUEOUS SYNTHESIS OF POLYSACCHARIDE-PROTEIN CONJUGATES FOR VACCINES

CROSS REFERENCE TO RELATED APPLICATION

This application claims priority to U.S. Provisional Application No. 61/385,673 filed Sep. 23, 2010, incorporated herein by reference.

FIELD OF INVENTION

The invention relates to a method of forming covalent bonds between a polysaccharide antigen and a protein to produce a polysaccharide-protein conjugate.

BACKGROUND OF INVENTION

The formation of polysaccharide-protein conjugates is of theoretical and practical interest (Oppenheimer, S. B., Alvarez, M. and Nnoli, J., 2008, Acta Histochemica, 110, 6-13, Ed.), (Seeberger, P. H. and Werz, D. B., 2007, Nature, 446, 1046-51, Ed.), (Bertozzi, C. R. and Kiessling L. L., 2001, Science, 29, 2357-64, Ed.) and is of particular interest in the synthesis of such conjugates for the production of carbohydrate vaccines. Carbohydrate vaccines for 26 diseases are currently being produced or under development (Astronomo, R. D. and Burton, D. R., 2010, Nat. Rev. Drug Discov., 9, 308-24, Ed.). What all these carbohydrate vaccines have in common is that the active immunogenic component is a polysaccharide-protein conjugate in which polysaccharide antigen from a pathogenic organism is coupled to a carrier protein. One of most commonly used carrier proteins for conjugation is Cross Reactive Material 197 ($CRM_{197}$), a non-toxic mutant of diphtheria toxin protein, tetanus toxoid, diphtheria toxin and tetanus toxin development (Astronomo, R. D. and Burton, D. R., 2010, Nat. Rev. Drug Discov., 9, 308-24, Ed.). The most commonly used polysaccharides are *Streptococcus pneumoniae* polysaccharide (PnPs), *Haemophilus influenze* polysaccharide, *Salmonella* polysaccharide, *Shigella* polysaccharide and *Neisseria meningitides* polysaccharide (Astronomo, R. D. and Burton, D. R., 2010, Nat. Rev. Drug Discov., 9, 308-24, Ed.), (Tan, L. K., Carlone, G. M. and Borrow, R., 2010, New Engl. J. Med., 362, 1511-20, Ed.). The covalent attachment of polysaccharide to a carrier protein in an efficient and cost-effective manner has proved challenging (Gildersleeve, J. C., Oyelaran, O., Simpson, J. T., and Allred, B., 2008, Bioconjugate Chemistry, 19, 1485-90, Ed.) and as a result the cost of carbohydrate vaccines greatly limits their use in developing countries (Astronomo, R. D. and Burton, D. R., 2010, Nat. Rev. Drug Discov., 9, 308-24, Ed.).

The most widely used methodology for making carbohydrate-protein conjugates for vaccines is reductive amination (Gildersleeve, J. C., Oyelaran, O., Simpson, J. T., and Allred, B., 2008, Bioconjugate Chem., 19, 1485-90, Ed.), (FIG. 1). In this procedure, the non-reducing polysaccharide is activated by the introduction of aldehyde groups by reaction with periodate (Kristiansen, K. A., Potthast, A. and Christensen, B. E., 2010, Carbohyd. Res., 345, 1264-1271, Ed.), (Perlin, A. S., 2006, 60, Adv. Carbohyd. Chem. Bi., 183-250, Ed.). The activated polysaccharide is then purified and mixed with the carrier protein in an aqueous solution. In this aqueous solution, reaction between the amino groups on the protein and aldehyde groups on the polysaccharide forms an unstable imine linkage between the protein and polysaccharide. Under aqueous conditions, reduction of the imine with cyanoborohydride (FIG. 1, reaction 3) is necessary to form a stable covalent linkage between the protein and the polysaccharide.

Several factors make the coupling of polysaccharide to proteins by aqueous reductive amination problematic. In water, the concentration of imine available for reduction by cyanoborohydride is very low for several reasons: 1) Water reacts with the aldehyde to form a lactol and the equilibrium between the lactol and free aldehyde on the activated carbohydrate (FIG. 1, reaction 4) favours the lactol thus greatly reducing the concentration of free aldehyde available for reaction with the amines on the protein to form imines. 2) The deprotonated form of the amine is required for reaction with the aldehyde, however at pH 8-9 only a small fraction of the amine groups are deprotonated. 3) The amount of iminium ion that can be formed is further reduced by the high concentration of water which prevents the formation of iminium ion (FIG. 1, reaction 2). For these reasons reductive amination is slow and inefficient and requires the use of high concentrations of sugar and long reaction times (Gildersleeve, J. C., Oyelaran, O., Simpson, J. T., and Allred, B., 2008, Bioconjugate Chem., 19, 1485-90, Ed.). In addition, the reducing reaction with cynanoborohydride (FIG. 1, reaction 3) results in cyanide contamination which must be removed. Due to procedural costs and the high cost of antigenic polysaccharide, the synthesis of polysaccharide-protein conjugates by reductive amination renders carbohydrate vaccines too expensive for general use in many parts of the world (Astronomo, R. D. and Burton, D. R., 2010, Nat. Rev. Drug Discov., 9, 308-24, Ed.)

There is a need for a methodology that eliminates these difficulties and provides a straightforward and cost-efficient method for synthesizing polysaccharide-protein conjugates.

SUMMARY OF INVENTION

The invention is a novel method of coupling polysaccharide antigens to proteins to produce polysaccharide-protein conjugates for carbohydrate vaccines.

According to one aspect of the invention, there is provided a method for the covalent attachment (conjugation) of polysaccharide to protein by use of a coupling reaction in a vacuum between a lyophilized mixture of activated polysaccharide antigen and protein.

According to another aspect of the invention, there is provided a method of covalent coupling of a non-reducing polysaccharide to a protein comprising the following steps:
providing a non-reducing polysaccharide;
activating the non-reducing polysaccharide to generate an activated polysaccharide having aldehyde groups; introducing a protein to provide an aqueous mixture of the activated polysaccharide and the protein; removing the water from the aqueous mixture by lyophilization to produce a dry lyophilized sample; sealing said dry lyophilized sample under a vacuum; incubating said dry lyophilized sample under vacuum at elevated temperature to cause a chemical reaction forming a protein-polysaccharide conjugate; or incubating said dry lyophilized sample under a dry inert gas at elevated temperature to cause a chemical reaction forming a protein-polysaccharide conjugate.

DESCRIPTION OF THE DRAWINGS

FIG. 1 is the reaction mechanism of the aqueous reductive amination method for covalently attaching activated polysaccharide to protein to form a conjugate. All the reactions are reversible except reaction 3. The mechanism shows how equilibria 2, 4 and 5 remove reactive species and decrease the amount of imine and therefore limit the amount of polysaccharide-protein conjugate that can be formed.

FIG. 2 is the reaction mechanism for the inventive non-aqueous vacuum coupling of polysaccharide to protein to form a conjugate.

FIG. 3 are HPLC profiles of $CRM_{197}$ before and after it had been subjected to the vacuum coupling procedure with PnPs 6A and PnPs 6B. The column eluate was monitored at 214 nm. The column was TOSOH Bioscience TSK gel 3000 $SW_{xL}$ and the running buffer was 50 mM phosphate pH 8. The broken vertical line designates the elution position of the unmodified control $CRM_{197}$.

Panel A—$CRM_{197}$ prior to vacuum conjugation.
Panel B—$CRM_{197}$ after vacuum conjugation with PnPs 6A
Panel C—$CRM_{197}$ after vacuum conjugation with PnPs 6B FIG. 4 are dried SDS-PAGE gels (resolving 10% acrylamide; 5% stacking; 1.5 mm thick) after staining. A: Coomassie Brilliant Blue. B: Periodate Acid Schiff (PAS)

All lanes contain 5 μg of $CRM_{197}$ except lane 2 which contains 2.5 μg

Lanes: 1—MW standards; 2—control $CRM_{197}$; 3—vacuum treatment of unactivated PnPs 6A with $CRM_{197}$; 4 & 5—duplicate vacuum conjugations of activated PnPs 6A with $CRM_{197}$; 6—control $CRM_{197}$; 7—vacuum treatment of unactivated PnPs 6B with $CRM_{197}$; 8 & 9—duplicate vacuum conjugations of activated PnPs 6B with $CRM_{197}$; 10—control $CRM_{197}$

DETAILED DESCRIPTION OF INVENTION

The inventive methodology provides a straightforward and cost-efficient method for synthesizing polysaccharide-protein conjugates. Polysaccharide is first activated with periodate, as in the aqueous reductive amination procedure. The invention is that the coupling of the activated polysaccharide to the protein can be accomplished more efficiently by lyophilizing a solution of the protein with the activated polysaccharide, sealing the dry lyophilizate in a vessel under vacuum and incubating the sealed vessel at an elevated temperature (FIG. 2). In the aqueous reductive amination procedure, stable covalent bond formation from the imine is driven by the chemical reactivity of the cyanoborohydride (FIG. 1, reaction 3). In contrast, in the inventive procedure, stable covalent bond formation occurs directly between the polysaccharide and protein and the driving force for conjugate formation is the release of $H_2O$ into the vacuum (FIG. 2). The reaction takes place with the protonated amine and, and unlike the aqueous reductive amination coupling procedure, there are no aqueous equilibria that remove reactive species and limit the amount of polysaccharide-protein conjugate that can be formed. In the absence of a strong reducing agent such as cyanoborohydride, glycation of proteins in aqueous solution takes place, albeit extremely slowly taking several days or weeks, by the reaction of a deprotonated amino group with a sugar aldehyde to form a ketoamine through the Amadori rearrangement (Isbell, H. S. and Frush, H. L, 1958, *J. Org. Chem.*, 23, 1309-1310, Ed.),
(Acharya, A. S., Roy, R. P. and Dorai, B., 1991, *J. Prot. Chem.*, 10, 345-348, Ed.). The inventive vacuum coupling reaction does not incorporate any reducing agent and the coupling reaction proceeds by the Amadori rearrangement to form a ketoamine in a matter of hours. The unexpected and surprising feature is that the reaction and rearrangement take place in the dry state under a vacuum, and the reaction occurs with the protonated amine not with the deprotonated amine as in the solution reaction, as shown in FIG. 2. The coupling reaction may also be performed by sealing the lyophilizate under a dry inert gas such as helium, neon, argon or nitrogen. This is accomplished by placing the lyophilizate under a vacuum and releasing the inert gas into the vacuum before sealing. The important factor is that there is no water present. The partial pressure of water is 0 so that the water released is effectively into a vacuum. Therefore, the driving force for the coupling re-action is the same as when the coupling is carried out in a vacuum in the absence of an inert gas.

The inventive vacuum conjugation procedure has the following advantages over the aqueous reductive amination procedure currently widely in use for the conjugation of antigenic polysaccharides to proteins to produce conjugates for carbohydrate vaccines: 1) High concentrations of polysaccharide are not required. 2) The reaction time is much shorter. 3) No chemicals are used in the conjugation reaction and therefore there is no need to remove cyanide or any other toxic contaminants from the conjugate product. 4) The absence of oxygen prevents the formation of advanced glycation end products and other contaminating oxidative products (Monnier, V. M. and Cerami, A., 1981, *Science*, 1981, 211, 491-493, Ed.). 5) The absence of water leads to a much higher conjugation efficiency. 6) The high conjugation efficiency and the requirement for less polysaccharide increase the cost-efficiency of conjugate preparation.

Experimental Protocol for the Non-Aqueous Synthesis of Polysaccharide-Protein Conjugates 1. Fragmentation of Polysaccharide The fragmentation of polysaccharide with acetic acid is a long established methodology used for fragmenting polysaccharides for the reductive alkylation procedure (6,8). For the in vacuo coupling procedure the established procedures can be used. Depending on the properties of the specific polysaccharide, fragments varying in size from 1 kDa to 500 kDa can be obtained by using concentrations of polysaccharide in the range of 1 mg/mL-10 mg/mL and acetic hydrolysis times in the range of 0.1 h to 24 h. The acetic acid can be removed by dialysis against distilled water using 3500 molecular weight cut-off (MWCO) tubing.

2. Activation of Polysaccharide

Activation of polysaccharide to introduce reactive aldehyde groups is an established methodology and routinely employed for the reductive alkylation coupling procedure (6,8,9,10). For the in vacuo coupling procedure the established procedures can be used. Sodium metaperiodate (0.5 M) is added to the solution of fragmented polysaccharide (5 mg/mL) in 100 mM phosphate pH 6.5 to a final concentration of 10 mM. After 2 h in the dark at 0° C., glycerol is added to a final concentration of 1%. The solution was dialyzed against distilled water using 3500 MWCO tubing.

3. Inventive Coupling reaction for Synthesis of Polysaccharide-Protein Conjugate i. A solution containing protein (5 mg/mL at pH 8) and periodate activated polysaccharide is prepared with a polysaccharide/protein ratio of 1:1 (w/w). The ratio can vary from 1:10 (w/w)-10:1 (w/w).

ii. The solution is adjusted to pH 8 and lyophilized.

iii. The lyophilizate is sealed under vacuum (20-50 mTorr) in a glass vessel.

iv. The sealed lyophilizate is incubated in an oven at 80° C. for 24 h. The temperature may vary from 40° C. to 120° C.

v. The vacuum is released and the polysaccharide-protein conjugate product and any unreacted material are dissolved in an aqueous solution.

vi. The polysaccharide protein product is separated from low molecular weight unreacted starting products and any by products by a molecular sieve filter with a cut off of 1 million kDa.

Example 1

Pneumococcal Polysaccharide (PnPs)

Materials

Pneumococcal Polysaccharide (PnPs), types 6A and 6B, and Cross Reactive Material 197 ($CRM_{197}$) were obtained from the Serum Institute of India. All other chemical, reagents and solvents were high purity preparations purchased from commercial sources.

Activation of Pneumococcal Polysaccharide (PnPs)

Typically, PnPs (6A or 6B at 5 mg/mL) was fragmented by hydrolysis in 100 mM acetic acid (6A for 18 h and 6B for 7 h) at 100° C. to produce polysaccharide of an average size of 30 kDa. Depending on the properties of the specific polysaccharide, fragments varying in size from 1 kDa to 500 kDa can be obtained by using concentrations of polysaccharide in the range of 1 mg/mL-10 mg/mL and acetic hydrolysis times in the range of 0.1 h to 24 h. The acetic acid was removed by dialysis against distilled water using 3500 molecular weight cut-off (MWCO) tubing. Sodium metaperiodate (0.5 M) was added to the solution of fragmented polysaccharide (5 mg/mL) in 100 mM phosphate pH 6.5 to a final concentration of 10 mM. After 2 h in the dark at 0° C., glycerol was added to a final concentration of 1%. The solution was dialyzed against distilled water using 3500 MWCO tubing.

Synthesis of Polysaccharide-Protein Conjugate

A solution containing $CRM_{197}$ (5 mg/mL at pH 8) and periodate activated PnPs 6A or 6B was prepared. Typically, the PnPs/$CRM_{197}$ ratio was 1:1 w/w but can vary from 1:10 (w/w)-10:1 (w/w). The solution was adjusted to pH 8 and lyophilized. The lyophilizate was sealed under vacuum (20-50 mTorr) in a glass vessel and incubated in an oven at 80° C. for 24 h; the temperature may vary from 40° C. to 120° C.

HPLC Analysis of Conjugates

FIG. 3 shows the HPLC absorbance profiles of $CRM_{197}$ at 214 nm before and after it had been subjected to the inventive vacuum coupling procedure with PnPs 6A and 6B. The control $CRM_{197}$ elutes after 8.4 minutes (FIG. 3A), but after the vacuum coupling procedure with PnPs 6A (FIG. 3B) and PnPs 6B (FIG. 3C) no $CRM_{197}$ appears in the profile as evidenced by the fact there is no absorbance peak at 8.4 min. A new protein absorbance peak at 214 nm appears at 5.5 minutes (FIGS. 3A and 3B). This peak occurs near the exclusion volume of the column which has an MW exclusion limit of 750 kDa and demonstrates the formation of high molecular weight polysaccharide-protein conjugates of PnPs 6A-$CRM_{197}$ and PnPs 6B-$CRM_{197}$.

SDS Gel Analysis of Conjugates

FIG. 4 shows SDS gels of the same conjugate preparations as in the HPLC analysis. FIG. 4a was stained with Coomassie Blue, a specific stain for proteins. Lanes 4 and 5 are duplicate PnPs 6A conjugate samples prepared according to the inventive vacuum coupling procedure described in the methods section above. The results demonstrate that after the vacuum coupling procedure no band staining at the position corresponding to $CRM_{197}$ (lanes 2,6 and 10) remains, confirming the HPLC analysis which also shows that no $CRM_{197}$ remains (FIG. 3B). There is also a new band appearing at the top of the resolving gel in lanes 4 and 5, consistent with a high molecular weight species corresponding to PnPs 6A-$CRM_{197}$ conjugate and also confirming presence of a high molecular weight species observed on HPLC analysis (FIG. 3B). Lane 3 shows the result when the vacuum coupling procedure was carried out with PnPs 6A which was not activated with periodate. There is a strong band present in the position of $CRM_{197}$ and no band corresponding to conjugate at the top of the gel. The results with PnPs 6B are identical to those with 6A. Lanes 8 and 9 show that no $CRM_{197}$ remains after the vacuum coupling procedure and a strong band at the top of the resolving gel corresponding to PnPs 6B-conjugate is present.

FIG. 4B is a duplicate gel of 4A which has been stained for the presence of carbohydrate with periodate acid Schiff reagent with p-rosaniline as the dye. Lanes 4 and 5 clearly show the presence of carbohydrate in the band at the top the resolving gel, which also stained for protein (FIG. 4A). There is also staining for carbohydrate in the loading wells. A close examination of FIG. 4A also shows staining for protein in the same locations. Therefore there is another high MW conjugate of PnPs 6a-CRM 197 that is formed. Similarly, lanes 8 and 9 in FIG. 4B show the same results and conclusions for the synthesis of PnPs 6B-$CRM_{197}$ conjugates, namely that two molecular weight categories of conjugate are produced by the vacuum coupling procedure, one of high MW>250 kDa and one of high MW>500 kDa.

In addition, to providing confirmatory evidence of the HPLC analyses (FIG. 3) of the vacuum coupling reactions of PnPs 6A and PnPs 6B to $CRM_{197}$, the SDS-PAGE gels in FIG. 4 provide further evidence of the stability of these conjugates. The preparatory procedure before applying samples to the gel requires heating of the sample for five minutes at 100° C. at pH 8 under denaturing condition in 2% SDS before loading the samples on the gel. The fact that these conjugates can be visualized on these gels and that no breakdown products are evident demonstrates that the ketoamine linkage between the polysaccharide and protein is extremely stable.

Conclusions

The results shown in FIG. 4 demonstrate that efficient synthesis of stable water-soluble polysaccharide-protein conjugates can be achieved by performing the coupling under vacuum. To achieve coupling between the polysaccharide and the protein, aldehyde groups are introduced into the polysaccharide to produce activated polysaccharide. The inventive reaction, as shown in FIG. 2, for the synthesis of polysaccharide protein conjugate occurs between amino groups on the protein and the aldehyde groups on the activated polysaccharide with the formation of a ketoamine linkage. Unlike the aqueous reductive amination procedure, the reaction forming the conjugate is not driven by the addition of a highly reactive chemical reagent but by the release of water into the vacuum. In the presence of dry inert gas, the release of water is effectively into a vacuum as no water is present. Incubation of the vessel, in which the lyophilizate is sealed under vacuum or dry inert gas such as nitrogen, helium, neon or argon, at elevated temperature greatly, accelerates the formation of conjugate.

There are at least three surprising and unexpected features of the invention: 1) Covalent bond formation between the protein and polysaccharide antigen of interest takes place under vacuum in the lyophilized state in the absence of water. 2) The coupling reaction takes place with the protonated form of the amino group not the expected deprotonated form of the amino group. 3) The covalent bond linking the protein and polysaccharide is a ketoamine. The inventive conjugation procedure has the following advantages over the aqueous reductive amination procedure currently widely in use for the conjugation of antigenic polysaccharides to proteins to produce conjugates for carbohydrate vaccines: 1) High concentrations of polysaccharide are not required. 2) The reaction time is much shorter. 3) No chemicals are used in the conjugation reaction and therefore there is no need to remove cyanide or any other toxic contaminants from the conjugate product. 4) The absence of oxygen prevents the formation of advanced glycation end products and other contaminating oxidative products. 5) The absence of water leads to a much higher conjugation efficiency. 6) The high conjugation efficiency and the requirement for less polysaccharide increase the cost-efficiency of conjugate preparation.

The foregoing is meant to be illustrative of the invention and not intended to limit it to the disclosed embodiments. Variations and changes obvious to one skilled in the art are intended to be within the scope and nature of the invention as defined in the claims.

The invention claimed is:

1. A method of covalent coupling of a non-reducing polysaccharide to a protein comprising the following steps:
    providing a non-reducing polysaccharide;
    activating the non-reducing polysaccharide to generate an activated polysaccharide having aldehyde groups at multiple interior sites of said non-reducing polysaccharide;
    introducing a protein to provide an aqueous mixture of the activated polysaccharide and the protein;
    removing the water from the aqueous mixture by lyophilization to produce a dry lyophilized sample;
    sealing said dry lyophilized sample under a vacuum or under an atmosphere of dry inert gas having low water vapour pressure;
    incubating said dry lyophilized sample or under an atmosphere of dry inert gas having low water vapour pressure under vacuum at elevated temperature to cause a chemical reaction forming a protein-polysaccharide conjugate.

2. A method according to claim 1 wherein said dry lyophilized sample is sealed under a dry inert gas.

3. A method according to claim 1 wherein the coupling of the polysaccharide with the protein is by means of a ketoamine covalent linkage.

4. A method according to claim 1 wherein the vacuum is between 100 mTorr and 10 mTorr.

5. A method according to claim 1 wherein the size of the polysaccharide is between 1 kDa and 1000 kDa.

6. A method according to claim 1 wherein the dry lyophilized sample is incubated in a vacuum at temperatures between 40° C. to 150° C.

7. A method according to claim 1 wherein the dry lyophilized sample is incubated in a vacuum in the absence of water and oxygen.

8. A method according to claim 6 wherein the dry lyophilized sample is incubated in a vacuum for between 1 h and 72 h.

9. A method according to claim 1 wherein the aqueous mixture has a pH of between 6 and 11.

10. A method according to claim 1 wherein the polysaccharide to protein ratio is between 1:10 (w/w) and 10:1 (w/w).

11. A method according to claim 1 wherein the polysaccharide is derived from pathogenic or non pathogenic organisms.

12. A method according to claim 1 wherein the inert gas is at least one of nitrogen, helium, neon or argon.

13. A method according to claim 1 wherein the coupling protein is diphtheria toxin, diphtheria toxoid or a mutant like $CRK_{197}$, tetanus toxin, tetanus toxoid or mutant thereof.

14. A method according to claim 1 wherein said polysaccharide is from an organism selected form the group consisting of streptococcus pneumoniae polysaccharide, *Haemophilus* influenzae polysaccharide, *Salmonella* species polysneeharide, *Shigella* polysaccharide and *Neisseria* meningitides.

15. A method according to claim 14 wherein said *Streptococcus* pneumoniae polysaccharide is capsular type 1, 2 and other serotypes used for polysaccharide vaccines and conjugate vaccine.

* * * * *